(12) United States Patent
Choi et al.

(10) Patent No.: US 10,864,238 B2
(45) Date of Patent: *Dec. 15, 2020

(54) **COMPOSITION CONTAINING *PORIA COCOS* PEEL EXTRACT FOR TREATING NEURODEGENERATIVE DISORDERS**

(71) Applicant: NeuroBo Pharmaceuticals, Inc., Boston, MA (US)

(72) Inventors: Sang Zin Choi, Suwon-si (KR); Mi Won Sohn, Yongin-si (KR); Hyo Sang Go, Seongnam-si (KR); Ja Young Ryu, Seoul (KR); Jin Seok Jeong, Seoul (KR); Song Hyen Choi, Suwon-si (KR); Eun Jin Kim, Seoul (KR); Young Woong Cho, Suwon-si (KR); So Young Kim, Seoul (KR)

(73) Assignee: NEUROBO PHARMACEUTICALS, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/535,478

(22) PCT Filed: Dec. 3, 2015

(86) PCT No.: PCT/KR2015/013136
§ 371 (c)(1),
(2) Date: Jun. 13, 2017

(87) PCT Pub. No.: WO2016/099056
PCT Pub. Date: Jun. 23, 2016

(65) Prior Publication Data
US 2017/0368122 A1 Dec. 28, 2017

(30) Foreign Application Priority Data

Dec. 19, 2014 (KR) .................. 10-2014-0184853

(51) Int. Cl.
*A61K 36/076* (2006.01)
*A61P 25/28* (2006.01)
*A61K 9/00* (2006.01)

(52) U.S. Cl.
CPC ............ *A61K 36/076* (2013.01); *A61P 25/28* (2018.01); *A61K 9/00* (2013.01)

(58) Field of Classification Search
None
See application file for complete search history.

(56) References Cited

U.S. PATENT DOCUMENTS

| 9,012,481 | B2 | 4/2015 | Hahn et al. |
| 10,588,927 | B2 | 3/2020 | Choi et al. |
| 2010/0184955 | A1 * | 7/2010 | Kim ...................... A61K 47/65 530/362 |
| 2010/0316741 | A1 * | 12/2010 | Kim ....................... A23L 2/02 424/728 |
| 2011/0319456 | A1 | 12/2011 | Hahn et al. |
| 2018/0256658 | A1 | 9/2018 | Choi et al. |

FOREIGN PATENT DOCUMENTS

| CN | 101152554 A | 4/2008 |
| CN | 102133351 A | 7/2011 |
| CN | 103393809 | 11/2013 |
| CN | 103393809 A | 11/2013 |
| CN | 102133242 A | 12/2013 |
| CN | 104013891 A | 9/2014 |
| EP | 1997902681 | 11/1999 |
| EP | 0970702 A1 | 1/2000 |
| EP | 2929888 A1 | 10/2015 |
| JP | 2012-514032 A | 6/2012 |
| JP | 2013234178 A | 11/2013 |
| KR | 10-2005-0092292 | 9/2005 |
| KR | 20050092292 A | 9/2005 |
| KR | 10-0526628 B1 | 11/2005 |
| KR | 20070111846 A | 11/2007 |
| KR | 10-2010-0070514 | 6/2010 |
| KR | 20100070514 A | 6/2010 |
| KR | 20110119983 A | 11/2011 |
| KR | 10-1251866 B1 | 4/2013 |
| KR | 10-2014-0074146 | 6/2014 |
| KR | 20140074146 A | 6/2014 |

(Continued)

OTHER PUBLICATIONS

Reitz "toward precision medicine in Alzheimer's disease" Ann Transl Med 4(6):107 (Year: 2016).*

(Continued)

*Primary Examiner* — Adam Weidner
(74) *Attorney, Agent, or Firm* — Sterne, Kessler, Goldstein & Fox P.L.L.C.

(57) ABSTRACT

The present invention relates to a pharmaceutical composition and a food composition for preventing or ameliorating degenerative neurological disease comprising *Poria cocos* peel extract for preventing, or treating neurodegenerative disorders. *Poria cocos* peel extract which is the active ingredients contained in the composition of the present invention, has a memory ameliorating activity through inhibiting of acetylcholine esterase and a neuroprotective effect and neuron protection by inhibiting the formation of beta amyloid and tau phosphorylation and promoting NGF production. Thus, the present invention may be useful as a pharmaceutical composition for preventing or treating degenerative neurological diseases, or as a health food for the above purpose.

14 Claims, 7 Drawing Sheets

(56) References Cited

FOREIGN PATENT DOCUMENTS

| WO | 1997-29764 | 8/1997 |
|---|---|---|
| WO | WO 9729764 A1 | 8/1997 |
| WO | WO-2009091130 A2 | 7/2009 |
| WO | WO-2014088200 A1 | 6/2014 |
| WO | WO-2016-099055 A1 | 6/2016 |

OTHER PUBLICATIONS

Stanford "Alzheimer's Prevention, Treatment and Research—A Q&A with Dr. Frank Longo" accessed from stanfordhealthcare.org on May 3, 2016 (Year: 2016).*
Chung "Neuroprotective Effect of a Chuk-Me-Sun-Dan on Neurons from Ischemic Damage and Neuronal Cell Toxicity" Neurochem Res 31(1):1-9 (Year: 2006).*
Machine translation of KR 20100070514, published Jun. 2010, received from STIC on Mar. 28, 2018 (Year: 2010).*
Borten "Chinese Herbs" accessed from chineseherbinfo on Feb. 7, 2019 (Year: 2012).*
Lee "Anti-inflammatory activity of the sclerotia of edible fungus, *Poria cocos* Wolf and their active lanostane triterpenoids" J funct food 32:27-36 (Year: 2017).*
Rios "chemical consituents and pharmacological properties of *Poria cocos*" planta med 77:681-691 (Year: 2011).*
Lin "traditional Chinese medicine for senile dementia" E-BCAM vol. 2012:13 pages (Year: 2012).*
Jean-Francois Emard et al., "Neurodegenerative Diseases and Risk Factors: A Literature Review", Soc. Sci. Med. vol. 40. No. 6, pp. 847-858, Mar. 1995.
Jean C. Augustinack et al., "Specific tau phosphorylation sites correlate with severity of neuronal cytopathology in Alzheimer's disease", Acta. Neuropathol., 103, 26-35, Published online: Oct. 26, 2001.
Lee et al., "Neurodegenerative Tauopathies", Annu. Rev. Neurosci., 24, 1121-1159, Mar. 2001.
Bergeron et al., "Cortical Degeneration in Progressive Supranuclear Palsy. A comparison with cortical_Basal Ganglionic degeneration", J. Neuropathol. Exp. Neurol., 56, 726-734, Jun. 1997.
Bugiani et al., "Frontotemporal Dementia and Corticobasal Degeneration in a Family with a P301S Mutation in Tau", J. Neuropathol. Exp. Neurol., 58, 667-677, Jun. 1999.
Delacourte et al.,"Vulnerable Neuronal Subsets in Alzheimer's and Pick's Disease Are Distinguished by Their T Isoform Distribution and Phosphorylation", Ann. Neurol., 43, 193-204, Feb. 1998.
Ittner and Gotz, "Amyloid-β and tau—a toxic pas de deux in Alzheimer's disease", Nat. Rev. Neurosci., 12, 67-72, Feb. 2011.
W. Fischer et al., "Amelioration of cholinergic neuron atrophy and spatial memory impairment in aged rats by nerve growth factor", Nature., Sep. 1987; 329(6134): 65-8.
M. Sendtner et al., "Brain-derived neurotrophic factor prevents the death of motoneurons in newborn rats after nerve section", Nature., Dec. 1992; 360(6406):757-9.
Hiroshi Mitsumoto et al., "Arrest of Motor Neuron Disease in wobbler Mice Cotreated with CNTF and BDNF", Science. Aug. 1994; 265(5175):1107-10.
Ling Hui, "Evaluation of the chemotherapeutic and chemopreventive potential of triterpenoids from *Poria cocos*", doctoral thesis of department of pharmacy, National University of Singapore, 2010.
Takaaki tai et al.,"Triterpenes from the surface layer of *Poria cocos*", Phytochem, vol. 39, No. 5, pp. 1165-1169, Jul. 1995.
Ying-Yong Zhao et al., "Urinary metabonomic study of the surface layer of *Poria cocos* as an effective treatment for chronic renal injury in rats", Journal of Ethnopharmacology, vol. 148, No. 2, 403-410, Available online Apr. 21, 2013.
Zhihong Lin et al., "Traditional Chinese Medicine for Senile Dementia", Evidence-Based Complementary and Alternative Medicine, 2012, vol. 2012, Article ID 692621, pp. 1~13, Published online Jul. 25, 2011.
Irina, Rastakhina, "Health and Beauty with NSP," published online on Nov. 23, 2008, accessed at http://nsp-leader.blogspot.ru/2008/11/nsp.html, accessed on Jul. 5, 2018, (Russian language document), 5 pages.
Irina, Rastakhina, "Health and Beauty with NSP," published online on Nov. 23, 2008, accessed at http://nsp-leader.blogspot.ru/2008/11/nsp.html, accessed on Jul. 5, 2018, 4 pages.
International Search Report and Written Opinion for International Application No. PCT/KR2015/013134, ISA/KR, Daejeon, Republic of Korea, dated Oct. 20, 2016, 11 pages.
International Search Report and Written Opinion for International Application No. PCT/KR2015/013136, ISA/KR, Daejeon, Republic of Korea, dated May 25, 2016, 11 pages.
May, B.H., et al., "Chinese Herbs for Memory Disorders: A Review and Systematic Analysis of Classical Herbal Literature," Journal of Acupuncture and Meridian Studies, 6:1; (Feb. 2013).
Park, Y.H., et al. "*Poria cocos* water extract (PCW) protects PC12 neuronal cells from beta-amyloid-induced cell death through antioxidant and antiapoptotic functions," Die Pharmazie: An International Journal of Pharmaceutical Sciences, 60:11 (2009).
Chung, T.W., "Neuroprotective Effect of a Chuk-Me-Sun-Dan on Neurons from Ischemic Damage and Neuronal Cell Toxicity," Neurochem Res 31(1):1-9 (2006).
Rios, J-L, "Chemical Constituents and Pharmacological Properties of *Poria cocos*,"Planta Med, 77:681-691 (2011).
Non-Final Office Action dated Dec. 4, 2018, in U.S. Appl. No. 15/535,489, Choi, et al., filed Jun. 13, 2017.
Final Office Action dated Jul. 16, 2019, in U.S. Appl. No. 15/535,489, Choi, et al., filed Jun. 13, 2017.
European Extended Search Report dated Jan. 8, 2020, in European Patent Application No. EP19210811.6, Munich, Germany, 8 pages.
Subash; S. et al., "Neuroprotective effects of berry fruits on neurodegenerative diseases," Neural Regen Res. 9(16): 1557-66, Wolters Kluwer, United States (Aug. 15, 2014).
Shih; P.H. et al. "Antioxidant and cognitive promotion effects of anthocyanin-rich mulberry (*Morus atropurpurea* L.) on senescence-accelerated mice and prevention of Alzheimer's disease," J. Nutri. Biochem.21:598-605, Elsevier, Netherlands (2010).
Wei; J. "Modern Research of Plant Medicine and Yunnan Famous Chinese Herbal Medicine," South 5 Yunnan Herbal, vol. 1, p. 659, Yunnan Science and Technology Press, First edition, (Mar. 2010).
Gu; K., "Healthy Diet Regimen for Patients with Cardiovascular and Cerebrovascular Diseases" p. 40, China Light Industry Press, First edition, (Jan. 2003).
Huang; T., "Business opportunities in food development of mulberry", China Agricultural Information 8:33, (2006).
Huang, H-P., et al., "Mulberry and its Bioactive Compounds, the Chemoprevention Effects and Molecular Mechanisms in Vitro and in Vivo," J. Tradit Complement Med 3(1):7-15(Jan-Mar. 2013).
Song, Z., et al., "The Isolation, Identification, and Determination of Dehydrotumulosic Acid in Poria cocos," Anal Sci 18(5):529-531, Japan Society for Analytical Chemistry, Japan (May 2002).
Zhongguo Zhongyao Zazhi, "Chemical Constituents of surface layer of Poria cocos and their pharmacological properties," STN, Caplus vol. 38, No. 7, pp. 1098-1102 (Apr. 2013).
Sandhya Joshi et al., "Classification of Neurodegenerative Disorders Based on Major Risk Factors Employing Machine Learning Techniques," International Journal of Engineering and Technology, vol. 2, No. 4, Aug. 2010.

* cited by examiner

COMPOSITION CONTAINING *PORIA COCOS* PEEL EXTRACT FOR TREATING NEURODEGENERATIVE DISORDERS

TECHNICAL FIELD

The present invention relates to a composition comprising *Poria cocos* peel extract for preventing, improving or treating neurodegenerative disorders.

RELATED ART

Degenerative neurological disease is a disease in which mental function is deteriorated due to gradual structural and functional loss of neurons. Degenerative neurological disease may be accompanied by symptoms such as dementia, extrapyramidal abnormality, cerebellar abnormality, sensory disturbance, and movement disorder due to nerve cell degeneration in specific areas of the nervous system. In addition, complex symptoms may occur due to multiple abnormalities at the same time. The disease is diagnosed according to the clinical manifestation of the patient. However, the symptoms vary widely, and different diseases often have common clinical symptoms, making diagnosis difficult (Soc. Sci. Med. Vol. 40. No. 6, pp. 847-858, 1995).

In degenerative neurological diseases, the symptom of the disease slowly develops, and the disease is often caused by aging. The disease progresses continuously for several years or decades until death, and thus increases the social burden. It has been known that genetic influences such as family history are very likely to be the cause of the disease, but acquired factors also play an important role. Degenerative neurological disorders can be classified according to their clinical symptoms, such as progressive dementia (Alzheimer's disease, etc.), neurological disorders (such as pick disease), posture and movement disorders (such as Parkinson's disease), progressive ataxia, and sensory and motor disorders (International Journal of Engineering and Technology, Vol.2, No.4, August 2010 Classification of Neurodegenerative Disorders Based on Major Risk Factors Employing Machine Learning Techniques).

Cytotoxicity of Aβ plaque and hyperphosphorylated tau tangle is attracting attention as a direct cause of Alzheimer's dementia, a typical degenerative brain disease.

Aβ is produced from the precursor APP and is produced outside the nerve cell by the action of enzymes such as β-secretase and γ-secretase. When Aβ concentrations are above a certain level, Aβ proteins bind to each other and form insoluble senile plaques. This substance can cause inflammation and neurotoxicity and destroy peripheral nerve cells. For example, it is known that neuronal death and microgranulosis observed in patients with Alzheimer's disease are associated with senile plaques. In vitro tests showed that Aβ peptide could induce activation of microglial cells (brain macrophages), which supports the hypothesis that Aβ peptides are cause of microencephalocytosis and brain inflammation found in the brain of patients with Alzheimer's disease. To date, there has been no widely accepted therapies or medicines that are expected to dissolve or prevent the formation of deposits once Aβ is formed and senile plaques are formed.

Tau consists of four parts: the N-terminal protruding portion, the proline aggregation domain, the microtubule binding domain and the C-terminal (Mandelkow et al., Acta. Neuropathol., 103, 26-35, 1996). It plays a role in connecting the microtubules that form the physical structure of nerve cells. It is known that tau is abnormally hyperphosphorylated or modified in the central nervous system neuronal cells to cause degenerative brain diseases such as tauopathy Alzheimer's disease, Picks disease, Frontotemporal dementia and parkinsonism linked to chromosome 17 are typical tauopathies (Lee et al., Annu. Rev. Neurosci., 24, 1121-1159, 2001; Bergeron et al., J. Neuropathol. Exp. Neurol., 56, 726-734, 1997; Bugiani et al., J. Neuropathol. Exp. Neurol., 58, 667-677, 1999; Delacourte et al., Ann. Neurol., 43, 193-204, 1998; Ittner and Gotz, Nat. Rev. Neurosci., 12, 65-72, 2011).

In the 1980s Alzheimer's study, neurotrophic factors were suggested to have therapeutic potential for degenerative neurological disorders(Nature. 1987 Sep. 3-9; 329(6134): 65-8. Amelioration of cholinergic neuron atrophy and spatial memory impairment in aged rats by nerve growth factor). Studies have shown that cholinergic neurons in the basal forebrain, lost due to aging, which is known to be one of the causes of Alzheimer's disease, are restored by administering nerve growth factor (NGF) to the lateral ventricle, resulting in an improvement in memory capacity of experimental animals. So, studies have been continuing to treat degenerative neurological diseases using neurotrophic factors. In a subsequent study, a study was carried out to restore motor nerve function by injecting Brain-derived neurotrophic factor (BDNF), Neurotrophin-3 (NT-3), Neurotrophin-4 (NT-4), and ciliary neurotrophic factor (CNTF), which are part of the neurotrophic factor family, into experimental animals that had impaired motor nerve function by nodulating the facial nerve and sciatic nerve, and positive results were obtained (Nature. 1992 Dec. 24-31; 360(6406):757-9. Brain-derived neurotrophic factor prevents the death of motoneurons in newborn rats after nerve section.). Furthermore, in the experiment using a recombinant mouse (wobbler) with a disease in which the number and function of motor neurons were gradually lost as aging progressed, the number of motor neurons was increased and the function was improved by administering BDNF and CNTF to the mice (Science. 1994 Aug. 19; 265(5175):1107-10. Arrest of motor neuron disease in wobbler mice co-treated with CNTF and BDNF). In addition to the above-mentioned studies, it has been reported that neurotrophic factors improve memory, cognition, and behavioral disorders in experimental animals by increasing the number and function of neurons in various sensory and motor neuropathic models.

The scientific name of Bokryeong (茯) is *Poria cocos*. *Poria cocos* is a plant of the class family Polyporaceae, in the order Aphyllophorales, in the class Eubasidiomycetes, Hymenomycetidae. *Poria cocos* is a kind of fungus belonging to *bacillus*, a brown rot fungus, which is a kind of saprophyte organism in the pine tree, but is also parasitic to the root of living pine tree. Mycelium grows while branching as a white color, and hyphae start to grow together. When the proper environmental conditions such as temperature and humidity are continued, hard lumps of sclerotia are formed. This is called bokryeong. According to the color of the inside, white is *poria cocos* wolf, rose pink is Jeok-bokryeong. The outer shell of *Poria cocos* is called *Poria cocos* peel.

The main components of the *Poria cocos* are Parchymic acid ($C_{33}H_{52}O_5$), Pinicolic acid ($C_{30}H_{18}O_3$), 3β-Hydroxy-lanosta-7.9(11), 24-Trien-21-oic acid and Tumulosic acid ($C_{31}H_{50}O$), Ebricoic acid ($C_{31}H_{50}O_3$), and the triterpene poricoic acid and its derivatives have been reported separately in the *Poria cocos* and *Poria cocos* peel. It also contains ergosterol, lecithin, adenine, choline, glucose, fructose and protein, and a large amount of inorganic substances, as well as purgiminic acid, evergreen acid, polytetanganic acid A and C and triterpenoids.

*Poria cocos* peel is sweet and the nature of *Poria cocos* peel is warm, and its taste and properties are all light, so it is said to be a medicinal substance with cool properties. In the past literature, it is described that the *Poria cocos* peel can relieve thirst, discharge urine smoothly, remove moisture, moderate body condition, enhance energy by harmonizing the function of digestive system, and improve circulation of abdominal extravagated blood by smoothing the waist. It was mainly used for prescription related to memory. In recent articles, anti-diabetic and anticancer effects of *Poria cocos* ha peel have been reported (Ling Hui, Evaluation of the chemotherapeutic and chemopreventive potential of triterpenoids from *Poria cocos*, Ling Hui, doctoral thesis of department of pharmacy, National University of Singapore, 2010).

*Poria cocos* peel is the outer shell of *Poria cocos* sclerotium belonging to the polyporaceae. It is known as a medicinal substance that has the effect to moderate edema by releasing water. Especially, it contains abundantly lorostane-based triterpene poricoic acid, and Donguibogam states that the *Poria cocos* peel is used as a component of Opisan (tangerine bark, arrecae pericarpium, ginger bark, morus alba bark) prescribed for edema. In recent studies, it has been reported that *Poria cocos* peel has therapeutic effects such as diuretic, urinary stimulation, edema reduction etc. (Triterpenes from the surface layer of *Poria cocos*, Takaaki tai, Phytochem, vol. 39, no. 5,1995; Urinary metabonomic study of the surface layer of *Poria cocos* as an effective treatment for chronic renal injury in rats, ying yong zhao et al, Journal of Ethnopharmacology, vol. 148, no. 2, s2013).

With this background, the inventors have conducted studies to develop materials for pharmaceutical composition and food compositions for the effective prevention, improvement and treatment of degenerative neurological diseases. As a result, the inventors of the present invention confirmed that these *Poria cocos* peel extracts exhibit significant memory recovery activity in a brain neuropathy model induced by various brain injury or memory-inhibiting drugs during a neuropsychological activity study of the *Poria cocos* peel. In addition, the present inventors have completed the present invention by confirming that these *Poria cocos* peel extracts have been shown to inhibit the production of substances that cause neuronal cell death in the brain and to protect the nerve cells by promoting the expression of proteins promoting neural cell regeneration and differentiation.

DETAILED DESCRIPTION OF THE INVENTION

Technical Problem

The objective of the present invention is to provide a pharmaceutical composition for preventing and treating degenerative neurological diseases and a food composition for preventing and improving degenerative neurological diseases, which contains of *Poria cocos* peel extract as an active ingredient.

Technical Solution

In order to achieve the above objective, the present invention provides a pharmaceutical composition for preventing and treating of degenerative neurological diseases, and a food composition for preventing and improving of degenerative neurological diseases, which contain *Poria cocos* peel extract.

Advantageous Effect

According of the present invention, *Poria cocos* peel extract inhibits the production of amyloid-$\beta$ (Abeta) and phosphorylation of tau, which may exhibit an effect of protecting nerve cells. In addition, it exhibits an effect of inhibiting acetylcholine esterase (AChE) to increase nerve conduction and to mediate memory enhancing action. Therefore, *Poria cocos* peel extract can be effectively used for the development of pharmaceutical compositions for preventing and treating degenerative neurological diseases including dementia or for the development of health food compositions for preventing and improving of degenerative neurological diseases.

MODE FOR INVENTION

Hereinafter, the present invention will be described in detail.

The present invention relates to a pharmaceutical composition for preventing or treating degenerative neurological diseases, comprising *Poria cocos* peel extract as an active ingredient.

*Poria cocos* peel extract according to the present invention can be provided according to a conventional method for preparing an herbal medicine extract, but specifically means an extract obtained by using water, alcohol, or a mixture of water and alcohol as a crude extract. The alcohol, which is one of the extraction solvents, may be, but is not limited to, a lower alcohol having 1 to 4 carbon atoms, preferably methanol, ethanol, butanol or alcohol spirit, more preferably ethanol. Here, the alcohol spirit means ethanol produced by fermenting starch raw material or saccharide raw material and distilling it. Furthermore, the mixed solvent of water and alcohol is not particularly limited, and may be mixed at any desired ratio.

In one embodiment of the present invention, *Poria cocos* peel extract may be extracted with 60 to 80% (v/v) ethanol, 65 to 75 (v/v)% ethanol or 70 (v/v) %, but is not limited thereto.

In a specific embodiment, *Poria cocos* peel extract of the present invention can be obtained as follows. First, the *Poria cocos* of the present invention are washed and dried, and then the dried herbal medicines are cut to obtain the cut herbal medicine. And water in an amount of 1 to 20 (v/w) times, preferably 5 to 10 (v/w) times, 1 to 4 carbon atoms lower alcohol or a mixture of water and lower alcohol having 1 to 4 carbon atoms, preferably 70 (v/v) % ethanol, is added to the dried cut *Poria cocos*. The mixture is subjected to extraction at a temperature of 10° C. to 100° C., preferably at room temperature for 1 to 72 hours, preferably for 48 hours by either cold extraction, hot water extraction, ultrasonic extraction, reflux cooling extraction, heat extraction, supercritical extraction, extraction with hot water extraction, preferably once by cold extraction, and concentrated under reduced pressure to produce *Poria cocos* peel extract.

The composition containing *Poria cocos* peel extract as an active ingredient according to the present invention can be used for the treatment of degenerative neurological diseases. Accordingly, the present invention provides a pharmaceutical composition for preventing and treating degenerative neurological diseases, which comprises *Poria cocos* peel extract as an active ingredient, uses *Poria cocos* peel extract for the preparation of a therapeutic agent for degenerative neurological diseases, and provides a method of treating degenerative neurological disease by administering to a subject a therapeutically effective amount of the *Poria cocos* peel extract.

As described above, the degenerative neurological disease according to the present invention means a degenerative disease of mental function caused by gradual structural and functional loss of nerve cells (neurons). Specifically, it includes diseases selected from the group consisting of Alzheimer's disease, Creutzfeldt-Jakob disease, Huntington's disease, multiple sclerosis, Guilin-Barre syndrome, Parkinson's disease, Lou Gehrig's disease, progressive dementia caused by gradual neuronal death and progressive ataxia.

In one embodiment of the present invention, the pharmaceutical composition for preventing and treating degenerative neurological diseases may contain *Poria cocos* peel extract as an active ingredient at an amount of 0.01 to 90 parts by weight, 0.1 to 90 parts by weight, 1 to 90 parts by weight, or 10 to 90 parts by weight of *poria cocos* .peel extract, based on 100 parts by weight of the total pharmaceutical composition, but is not limited thereto, and may vary depending on the condition, the type and progress of disease.

In another embodiment of the present invention, the pharmaceutical composition for preventing and treating degenerative neurological diseases containing *Poria cocos* peel extract as an active ingredient may be formulated into pharmaceutical preparations for the prevention and treatment of degenerative neurological disorders, including pharmaceutically acceptable carriers, diluents or excipients.

Examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil.

Also, the composition of the present invention may be formulated into pharmaceutical compositions in the form of powders, granules, tablets, capsules, suspensions, emulsions, oral preparations such as syrups and aerosols, external preparations, suppositories or sterilized injection solutions. In general, in the case of formulation, it can be prepared by using commonly used diluents such as a filler, an extender, a binder, a wetting agent, a disintegrant, a surfactant, or an excipient. Solid form preparations for oral administration include tablets, pills, powders, granules, capsules and the like, which may contain at least one excipient such as starch, calcium carbonate, sucrose, lactose, gelatin and the like. In addition to simple excipients, lubricants such as magnesium stearate and talc may also be used. Examples of liquid formulations for oral use include suspensions, solutions, emulsions and syrups, and various excipients such as wetting agents, sweeteners, fragrances, preservatives, etc. in addition to commonly used simple diluents such as water and liquid paraffin. Formulations for parenteral administration include sterilized aqueous solutions, non-aqueous solutions, suspensions, emulsions, freeze-dried preparations and suppositories. Examples of the suspending agent include propylene glycol, polyethylene glycol, vegetable oil such as olive oil, injectable ester such as ethyl oleate, and the like. Examples of the suppository base include witepsol, macrogol, tween 61, cacao butter, laurinum, and glycerogelatin.

The dosage of the pharmaceutical composition for the prevention and treatment of degenerative neurological diseases containing *Poria cocos* peel extract as an active ingredient of the present invention may vary depending on the age, sex, and body weight of the patient, Generally, an amount of 0.1 to 100 mg/kg, preferably 1 to 30 mg/kg, may be administered once to several times per day. The dosage may also be increased or decreased depending on the route of administration, degree of disease, sex, body weight, age, health condition, diet, administration time, administration method, excretion rate and the like. Accordingly, the dose is not intended to limit the scope of the invention in any way.

The pharmaceutical composition for the prevention and treatment of degenerative neurological diseases containing *Poria cocos* peel extract of the present invention can be administered in various routes to mammals such as rats, mice, livestock, and humans. All modes of administration may be expected, for example, by oral, rectal or intravenous, intramuscular, subcutaneous, intra-uterine dural or intracerebral injection.

The *Poria cocos* peel extracts of the present invention has little toxicity and side effects, and therefore can be safely used for long-term use for preventive purposes.

The present invention also provides a food composition comprising *Poria cocos* peel extract. *Poria cocos* peel extract inhibits the production of substances causing neuronal cell death in the brain, promotes the expression of proteins promoting neural cell regeneration and differentiation to protect nerve cells and can be effectively used for the production of health functional food and general food which can exhibit the effect of preventing and improving neurodegenerative diseases in particular.

Specifically, the health functional food defined in the present invention is defined as "a health food which is on the list of Regulations Regarding Health Functional Food Ingredients or Recognition of Ingredients regulated in the Korea Food and Drug Administration's Notice 2004-12 after having fully established functionality and safety in the human body," which was newly defined through the "Regulation on Health Functional Foods in 2002".

The food composition containing the extracts of *Poria cocos* peel according to the present invention can be used in various foods for symptom relief of degenerative neurological diseases. Foods to which the herbal medicine extract of the present invention can be added are various foods such as beverages, gums, tea, vitamin complex, health functional foods, and health functional beverages, and they can be used in the form of pills, powders, granules, infusions, tablets, capsules or beverages.

The amount of *Poria cocos* peel extract in the health food composition is generally 0.1 to 15 wt %, preferably 0.2 to 10 wt %, and in the case of the health beverage composition, 0.1 to 30 g, preferably 0.2 to 5 g, based on 100 mL, may be included.

When the food composition according to the present invention is prepared in a beverage form, there are no particular restrictions on the liquid ingredients other than those containing the herbal extracts as essential ingredients in the proportions indicated. In addition, various flavoring agents or natural carbohydrates may be added as an additional ingredient, such as ordinary beverages.

Examples of the above-mentioned natural carbohydrates include monosaccharides such as glucose and fructose; Disaccharides; such as maltose, sucrose and the like, Polysaccharides; Dextrin, cyclodextrin and the like, or sugar alcohols such as xylitol, sorbitol and erythritol. As natural flavors other than those mentioned above, natural flavoring agents (tautatin, stevia extract (e.g., rebaudioside A, glycyrrhizin etc.)) and synthetic flavors (saccharin, aspartame, etc.) can be advantageously used. The ratio of the natural carbohydrate is generally about 1 to 20 g, preferably about 5 to 12 g per 100 ml of whole health beverage composition.

In addition to the above description, the food composition of the present invention may further contain various additives such as various nutrients, vitamins, minerals (electrolytes), flavorings such as synthetic flavors and natural flavors, colorants and thickeners (cheese, chocolate, etc.) pectic acid and its salts, alginic acid and its salts, protective colloid thickening agents, pH adjusting agents, stabilizers, preservatives, glycerin, alcohols, carbonating agents used in carbonated drinks, and the like. In addition, the compositions of the present invention may contain natural fruit juice and pulp for the production of fruit juice drinks and vegetable drinks. These components can be used independently or in combination. The ratio of such additives is not particularly limited, but is generally selected in the range of 0 to about 20 parts by weight per 100 parts by weight of the total food composition of the present invention.

In another embodiment, the present invention is a method for preventing, improving or treating a degenerative neurological disease, comprising administering a composition containing an active ingredient of *Poria cocos* peel extract. Alternatively, the present invention provides a use of *Poria cocos* peel extract for preventing, improving or treating a degenerative neurological disease. The dose, dosage form, administration method, etc. of the composition containing *Poria cocos* peel extracts for such method or use are as mentioned above.

MODE OF THE INVENTION

The present invention will be explained in detail with reference to the following examples and experiments. However, the following examples and experiments are only to illustrate the present invention, and the scope of the present invention is not limited thereto.

EXAMPLE 1

Preparation of *Poria cocos* Peel Extract of the Present Invention

Dried *Poria cocos* peel were purchased at a herbal medical store in Kyungdong market and contaminants were removed and well-dried herbal medicine was used for the experiment. *Poria cocos* peel cut in an amount of 100 g was mixed with 1 L distilled water (DW), 30, 50, 70, or 95 (v/v) % aqueous ethanol solution and the mixture was kept at room temperature for 48 hours. After filtration, the mixture was concentrated under reduced pressure, and then lyophilized to obtain *Poria cocos* peel extracts (crude extracts) to give Example 1 (See Table 1).

TABLE 1

Preparation of *Poria cocos* peel extracts according to the present invention

| | Raw material amount (g) *Poria cocos* peel | Solvent selection | Amount of solvent | Extraction temperature | Extraction time | Product(g) | Yield(%) |
|---|---|---|---|---|---|---|---|
| Example 1 | 100 g | DW | 1 L | Room temperature | 2 days | 7.32 | 7.32 |
| | 100 g | 30% EtOH | 1 L | Room temperature | 2 days | 6.59 | 6.59 |
| | 100 g | 50% EtOH | 1 L | Room temperature | 2 days | 7.02 | 7.02 |
| | 100 g | 70% EtOH | 1 L | Room temperature | 2 days | 6.93 | 6.93 |
| | 100 g | 95% EtOH | 1 L | Room temperature | 2 days | 5.43 | 5.43 |

EXAMPLE 1

Test of Memory Improvement and Nerve Cell Protection Effect of *Poria cocos* Peel <1-1>Preparation of Experimental Animals Scopolamine Induced Memory Impairment Six-week-old ICR mice were used for the experiment and each experimental group consisted of 8 animals.

After 30 minutes of administering the *Poria cocos* peel extract and comparative drug, 1 mg/kg scopolamine was intraperitoneally administered (i.p). Normal animals were injected with the same amount of physiological saline.

Behavioral studies were performed after 30 minutes of scopolamine administration.

Aβ Infusion Model

Six-week-old ICR mice were used in the experiment. The animals were anesthetized, fixed in a stereotaxic apparatus (Stoelting) and injected with 3 uL of vehicle (artificial CSF) or $A\beta_{42}$ for 6 minutes using a Hamilton micro syringe (fitted with a 26-gauge needle).

Animals treated with $A\beta_{42}$ were randomly divided into experimental groups. From 2 days after administration of $A\beta_{42}$, the experimental drug and the positive control drug (Donepezil) were administered once a day for 11 days.

The lyophilized drug, ethanol extracts of *Poria cocos* peel and control drug were suspended in 3% HPMC aqueous solution, and all the drugs were prepared on the day of the experiment.

Measurement of Protein in Brain

To examine the efficacy of *Poria cocos* peel extracts on the production of nerve cell death inducer or substances involved in cell protection, six weeks old ICR mouse were administered *Poria cocos* peel extract and the control drug for 5 days. On the 5th day 4 hours after the administration, experimental animals were sacrificed and the brain was separated. The hippocampus region was separated and used for protein analysis. Protein assay was performed to quantify the total protein content in the sample. The measured values were expressed as the measured value per unit protein.

<1-2>Passive Avoidance Task

Passive avoidance experiments were performed in two independently separated bright and dark square boxes. Bright areas (20×20×20 cm) were illuminated with 50 W incandescent lamps. Light and dark areas (20×20×20 cm) were spaced 1 cm apart and 2 mm stainless steel rods were installed.

In the habituation phase, the two sections were separated by a guillotine door (5×5 cm), and the guillotine door was opened after 30 seconds after placing the experimental animals in the light section. The animals were allowed to freely navigate. When they reached the dark area, the guillotine door was closed and the animals were taken out after 3 seconds.

Acquisition trials were conducted 24 hours later. After 30 minutes of drug and control drug administration, 1 mg/kg of scopolamine was intraperitoneally administered and 30 minutes later, the behavioral experiment was performed. The experimental mice were initially placed in the bright zone and the door between the zones was opened after 30 seconds. When the experimental mice entered the dark area, the guillotine door was closed, an electrical foot shock was immediately applied through a stainless steel rod for 2 seconds at 0.5 mA intensity, and the time for the experimental animals to enter the dark zone was measured After performing the acquisition trials and giving a 24-hour rest period, the experimental animals were placed in a bright area for measuring the retention trial and the time until entering the dark area was measured. Both the acquisition trial and the retention trial were performed to determine the time taken for the mouse to enter all four paws in a dark room from a bright room.

Figure 1:
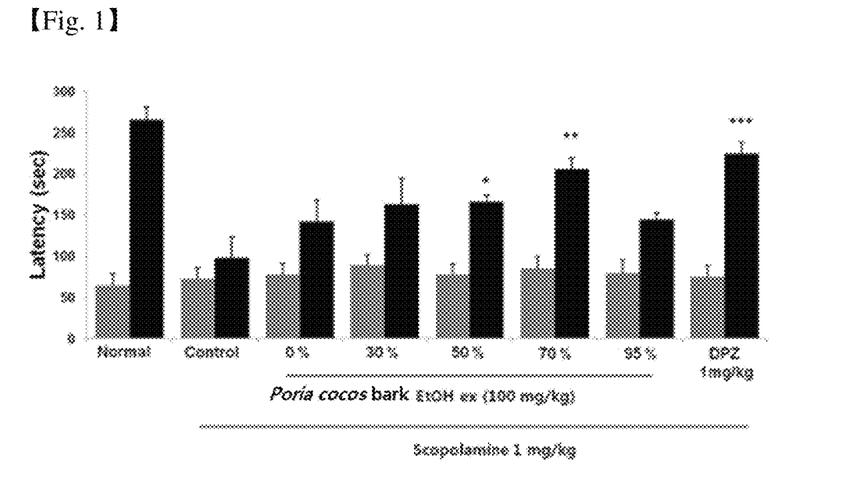
FIG. 1 is a graph showing the results of a passive avoidance test in an experimental animal model in which memory formation was inhibited by scopolamine after treating with *Poria cocos* peel extract.

As a result, as shown in FIG. 1, it was confirmed that a significant effect of improving spatial memory was obtained when *Poria cocos* peel ethanol extracts of 0, 30, 50, 70, and 95 (v/v) % were orally administered. The most potent 70% ethanol extract of *Poria cocos* peel showed similar efficacy to Donepezil (DPZ) 1 mg/kg, which is known as acetylcholinesterase inhibitor (FIG. 1).

<1-3>Y-Maze Test

The Y-maze experiment was conducted to investigate the effect of short-term memory. The animals were placed on one arm of the Y-maze and allowed to move freely for 8 minutes. Spontaneous alternation and total number of entries were measured. When the animals consecutively entered into three arms, they were defined as alternation entry, and the ratio was calculated by the following equation 1.

Spontaneous alternation ratio (%)=[(number of changes)/(total number of arm entry −2)]×100  [Equation 1]

Figure 2:
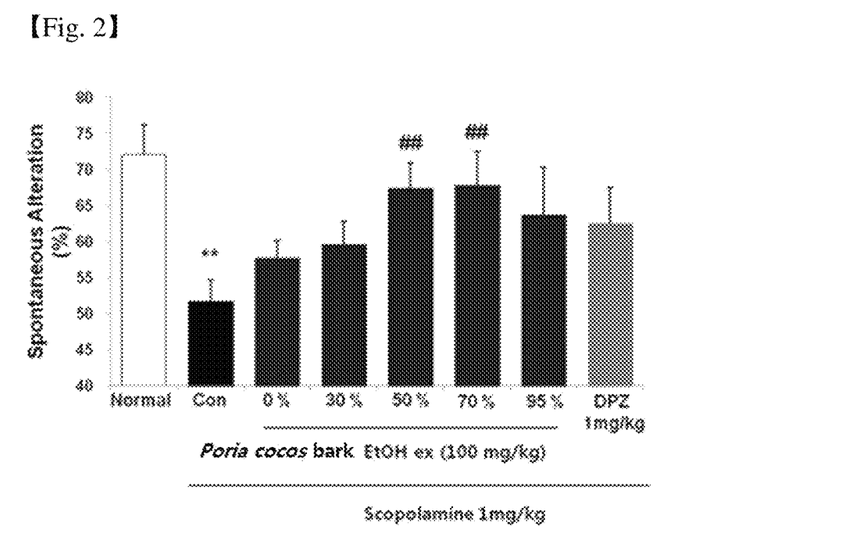
FIG. 2 is a graph showing the results of the Y-maze task in an experimental animal model in which memory formation was inhibited by scopolamine after treating with *Poria cocos* peel extract.
Figure 4:
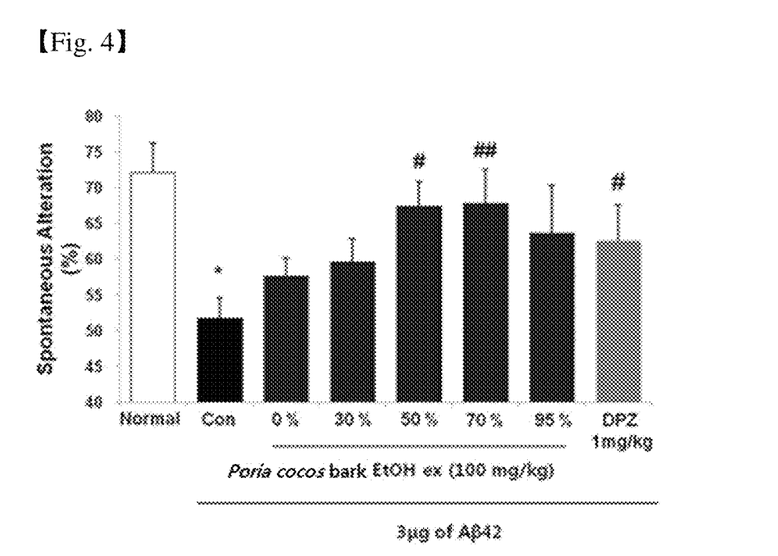
FIG. 4 is a graph showing the results of the Y-maze task when *Poria cocos* peel extract was treated in an animal model in which beta amyloid was infused into the brain to induce symptoms of Alzheimer's dementia.

As a result, as shown in FIG. 2, the oral administration of ethanol extracts of 0, 30, 50, 70, and 95 (v/v) % *Poria cocos* peel at a dose of 100 mg/kg resulted in improvement of spatial memory in the scopolamine-induced experimental animal model in which memory formation was inhibited. And as shown in FIG. 4, spatial memory was also restored in the $A\beta_{42}$—administered Alzheimer's dementia model (FIGS. 2 and 4).

<1-4>Novel Object Recognition (NOR) Task

Inside a black box of 45 cm width, 45 cm length and 50 cm height, two plastic objects of the same size but different shapes were placed. The experimental animals were allowed to move freely for 8 minutes and the time spent on each object was measured (training session). 24 hours later, the experimental animals were placed in a box with one familiar object from the training session and one new object, and the time spent in each object was measured (test session). The recorded values were calculated using the following equation (2), which is expressed as a recognition result of a new object.

Recognition rate of new objects (%)=Time spent on new objects/(Time spent on new objects+Time spent on experienced objects)×100  [Equation 2]

Figure 3:
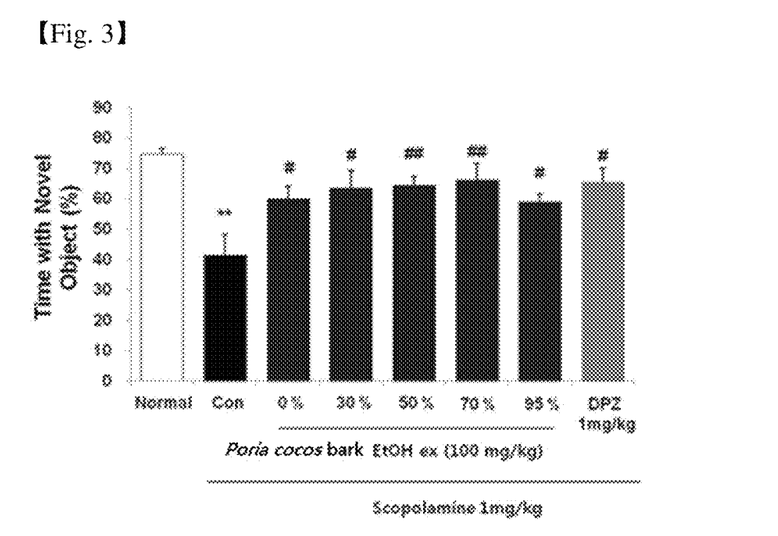
FIG. 3 is a graph showing the results of the Novel object recognition (NOR) task in an experimental animal model in which memory formation was inhibited by scopolamine after treating with *Poria cocos* peel extract.
Figure 5:
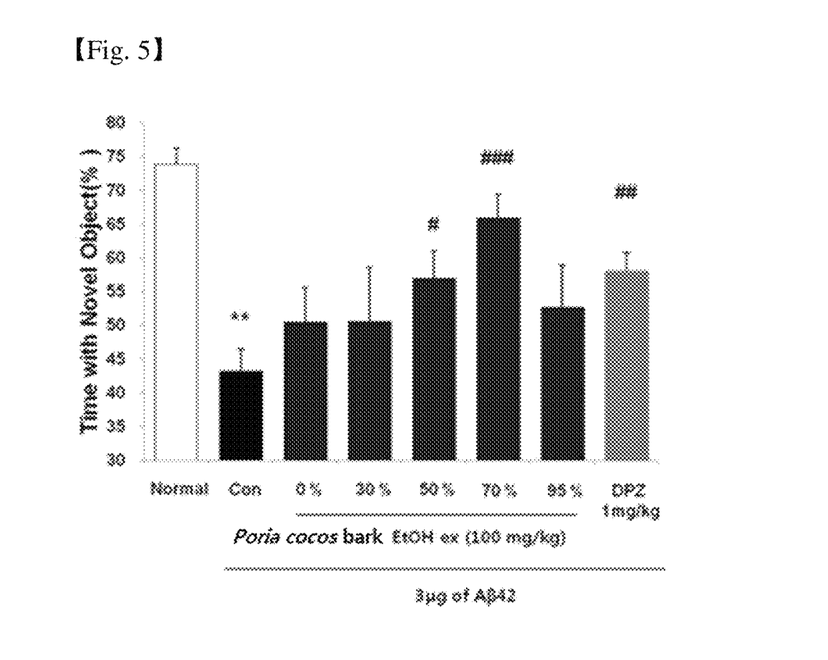
FIG. 5 is a graph showing the results of a Novel object recognition task (NORT) when *Poria cocos* peel extract was treated in an animal model in which beta amyloid was infused into the brain to induce symptoms of Alzheimer's dementia.

As shown in FIG. 3, when *Poria cocos* peel 0, 30, 50, 70, and 95% ethanol extracts at a dose of 100 mg/kg was orally administered, the scopolamine-induced experimental animal model in which memory formation was inhibited showed cognitive memory improvement. As shown in FIG. 5, Alzheimer's dementia model due to administration of $A\beta_{42}$ also restored cognitive memory (FIG. 3, 5).

<1-5>Immunohistochemical Staining

For immunohistochemical staining, the Aβ infusion animal described in Experimental Example 1-1 was perfused with 1×PBS (phosphate buffered saline), fixed with 4% paraformaldehyde, and brain was extracted. The brain was fixed in the same solution for one day and stored in a 30% sucrose solution and the solution was changed every two days until frozen at 4° C. After that, brain tissue was frozen sufficiently at −20° C. by dropping OCT (optimal cutting temperature) compound in a cryostat, and then made into a 30 μm thick section, and stored at 4° C. in a preservative solution. Immunohistochemical staining was performed with the hippocampus region. The tissues washed with PBS were treated with 1% $H_2O_2$ for 15 minutes, After that, the tissues were treated with 0.05 M PBS, 1.5% normal goat serum, 0.5 mg/ml bovine serum albumin, 0.3% triton X–100 and goat NeuN primary antibody (1: 500), and were reacted at 4° C. for 24 hours to prevent nonspecific reactions. After the primary antibody was removed, the tissue was reacted with a peroxidase-conjugated secondary antibody (1: 200) for 90 minutes, and the ABC was diluted in the buffer and allowed to react at room temperature for about 1 hour. After washing three times with PBS, the tissue was developed with 0.02% DAB and 0.01% $H_2O_2$ and subjected to ethanol and xylene dehydration to prepare slide samples.

Figure 6:
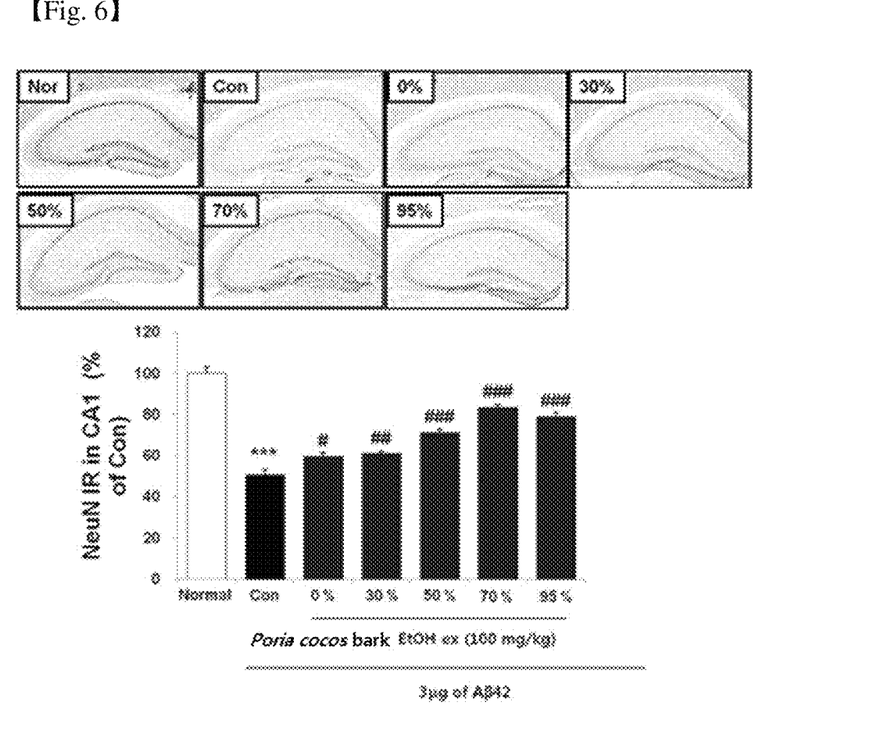
FIG. 6 is a graph showing the results of neuronal cell staining when *Poria cocos* peel extract was treated in an animal model in which beta amyloid was infused into the brain to induce Alzheimer's dementia symptoms.

As a result, as shown in FIG. 6, when *Poria cocos* peel 0, 30, 50, 70, and 95 (v/v)% ethanol extracts at a dose of 100 mg/kg was orally administered, neurons (NeuN positive) decreased by beta amyloid toxicity were significantly increased (FIG. 6). It was confirmed that *Poria cocos* peel extract has a protective effect on neuronal cells and can increase memory capacity.

<1-6 >Measurement of Aβ Production in Brain

ELISA experiments were conducted to investigate the inhibitory effect of *Poria cocos* peel extracts on beta amyloid production, which is known to be a major cause of Alzheimer's disease.

The brain of normal animals in Experimental Example <1-1>was extracted, and Ripa buffer was added and homogenized mechanically. After centrifugation, the supernatant was taken and beta amyloid (IBL) concentration was measured. The amount of Aβ1340 expression in 1 mg protein was measured.

Figure 7:
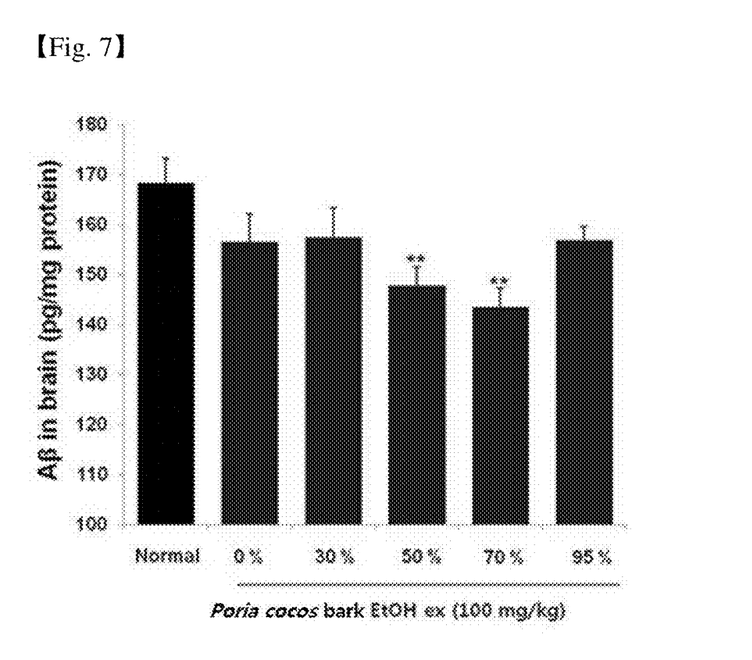
FIG. 7 is a graph showing the results of beta amyloid measurement after treating the normal animal with *Poria cocos* peel extract.

As a result, as shown in FIG. 7, the brain beta-amyloid concentration was significantly decreased when 100 mg/kg *Poria cocos* peel ethanol extract of 0, 30, 50, 70, 95 (v/v) (FIG. 7) was orally administered. From the above results, it was confirmed that *Poria cocos* peel extract removed beta amyloid, which is a cause of Alzheimer's dementia.

<1-7 >NGF (Nerve Growth Factor) Level Measurement

ELISA experiments were conducted to confirm the efficacy of *Poria cocos* peel extract on NGF production, known to have a neuronal regeneration and differentiation activity. After the brains of normal animals in Experimental Example <1-1>were extracted, the hippocampal region was separated, and RIPA buffer was added thereto and mechanically homogenized. For NGF measurement, a high salt high detergent buffer corresponding to the weight of each brain was added and mechanically homogenized. After adding 10 uL of 4N HCl and allowing to stand for 15 minutes, NGF bound to the receptor was dissociated, 4N NaOH was added, and the mixture was allowed to stand for another 15 minutes. The supernatant was taken by centrifugation and the NGF concentration in the brain was measured using an NGF measurement kit (Millipore).

Figure 8:
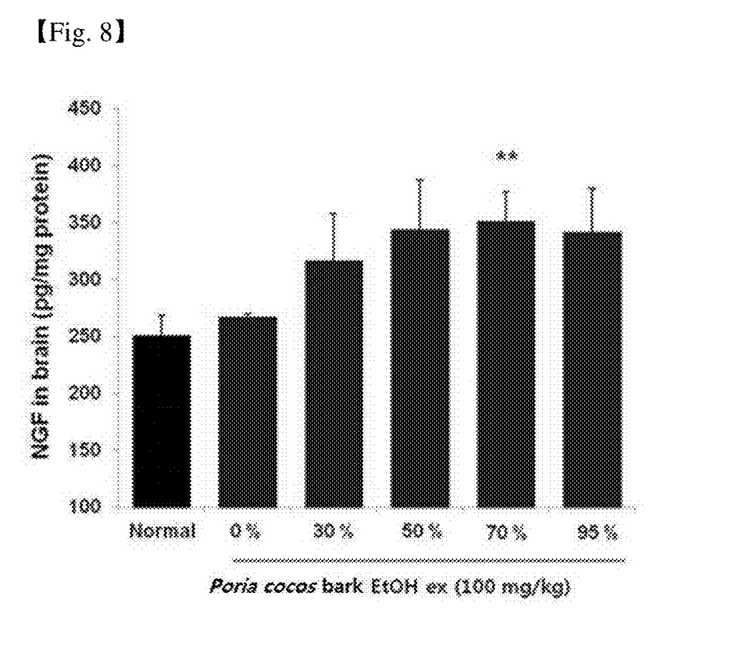
FIG. 8 is a graph showing the results of measurement of NGF production after treating the normal animal with *Poria cocos* peel extract.

As a result, as shown in FIG. 8, NGF concentration in the brain was significantly decreased when 100 mg/kg of ethanol extracts of 0, 30, 50, 70, and 95% was orally administered. These results suggest that *Poria cocos* peel extract promotes nerve cell protection by promoting NGF production.

EXAMPLE 2

Confirmation of in vitro Neuroblastoma Protective Effect of *Poria cocos* Peel Extracts <2-1 >Measurement of acetylcholinesterase (AChE) Activity in Nerve Cell Lines Various acetyl cholinesterase inhibitors have been developed and used because they enhance memory capacity and improve dementia by activating cholinergic neurons by increasing the acetylcholine concentration in the ganglion neurotransmitter. Acetyl cholinesterase activity was measured to confirm the acetyl cholinesterase inhibitory effect of *Poria cocos* peel extract. SH-SY5Y cells, a neuronal cell line, were purchased from KCLB (Korean Cell Line Bank). SH-SY5Y cells ($1 \times 10^6$ cells/well) were inoculated on 6-well culture plates and cultured in DMEM/F12 (Dulbecco's modified Eagle's medium) medium containing 10% fetal bovine serum for 48 hours. After 5 days of differentiation using DMEM/F12 medium containing 10 μM retinoic acid and 3% FBS, the cells were treated with *Poria cocos* peel extract (10, 100 μg/ml). Cell lysis was performed using RIPA buffer (150 mM NaCl, 0.5% Triton X-100, 50 mM Tris-HCl, pH 7.4, 25 mM NaF, 20 mM EGTA, 1 mM DTT, 1 mM $Na_3VO_4$, protease inhibitor cocktail), and protein content was quantitated with BCA reagent purchased from Pierce. The acetylcholinesterase enzyme activity was determined by acetylcholine as a substrate according to the Ellman method. The resulting thiocholine produced by acetyl cholinesterase was reacted with DTNB and the resulting 5-thio-2-nitrobenzoate was determined by measuring the absorbance change at 405 nm.

Figure 9:
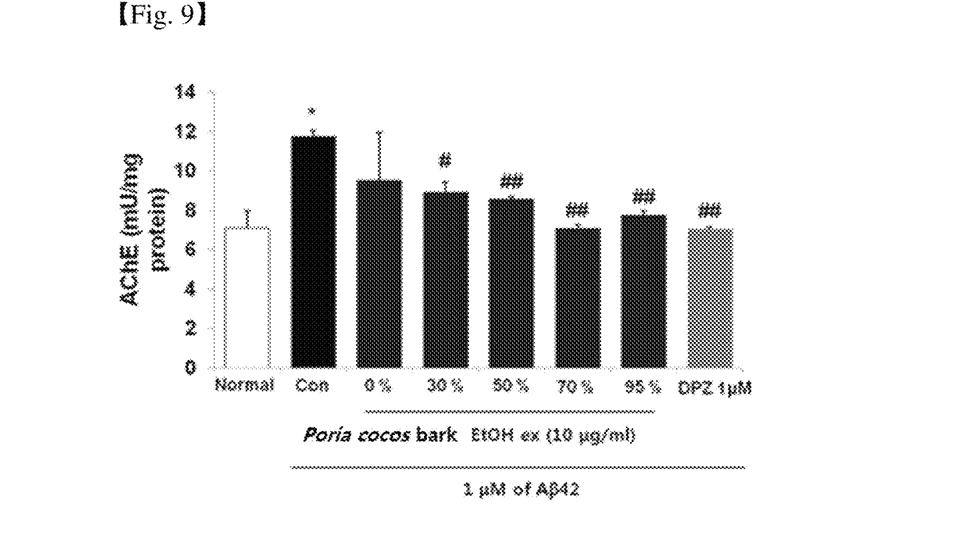
FIG. 9 shows the result of measuring the AChE activity after treating the neural cell line SH-SY5Y with *Poria cocos* peel extract.

As a result, as shown in FIG. 9, when the ethanol extracts of *Poria cocos* peel 0, 30, 50, 70, 95 (v/v) % were administered to nerve cell lines at a concentration of 10 μg/ml, $Aβ_{42}$—induced acetyl cholinesterase activity was restored to normal level (FIG. 9).

<2-2 >Cell Protection Effect in Nerve Cell Line

The cytoprotective effect of *Poria cocos* peel extracts was measured using a MTT(3-(4,5-Dimethylthiazol-2-yl)-2,5-Diphenyltetrazolium Bromide) assay in a model that causes toxicity to nerve cell lines by substance that artificially aggregates Aβ42. SH-SY5Y cells ($1 \times 104$ cells/well) were inoculated into 96-well culture plates and cultured in DMEM/F12 (Dulbecco's modified Eagle's medium: nutrient mixture F-12) containing 10% fetal bovine serum for 48 hours. After 5 days of DMEM/F12 medium containing 10 μM retinoic acid and 3% FBS, the cells were treated with *Poria cocos* peel extract was treated at a concentration of 0.01, 0.1, 1, 10, 100 or 200 μg/ml and left for 6 hours. Thereafter, $Aβ_{42}$ was treated and cultured for a total of 48 hours. After 4 hours of treatment with 2 mg/ml MTT, Formazone was dissolved in DMSO and absorbance was measured at 590 nm.

Figure 10:
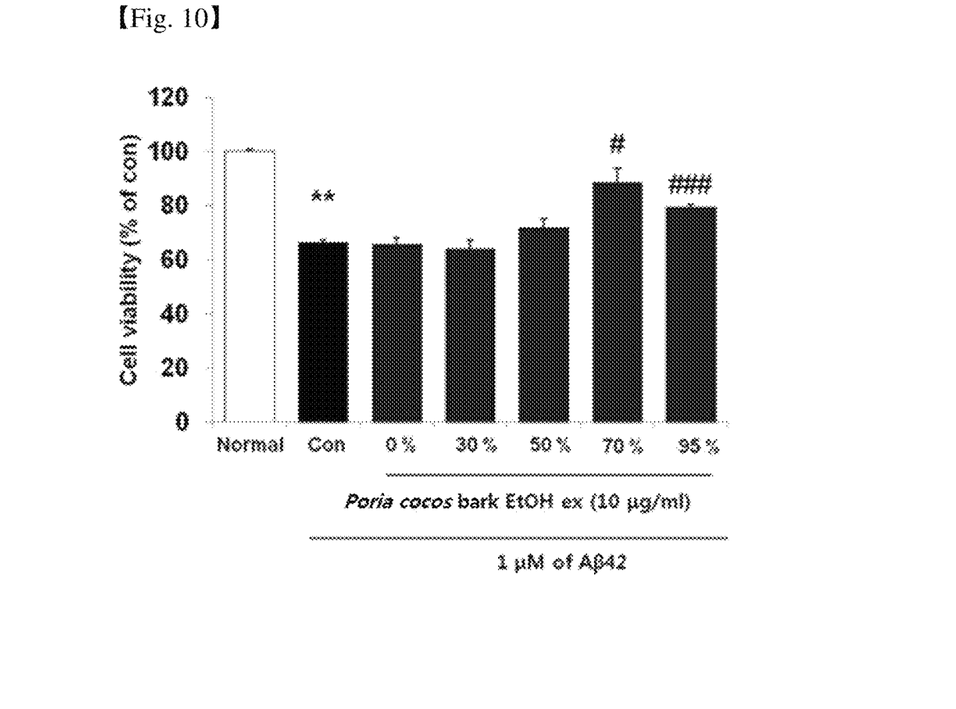
FIG. 10 shows the results of measuring the degree of apoptosis by MTT assay after treating the neural cell line SH-SY5Y with *Poria cocos* peel extract.

As shown in FIG. 10, $Aβ_{42}$—induced cytotoxicity decreased in a concentration-dependent manner following administration of 10 μg/ml of *Poria cocos* peel ethanol extracts of 0, 30, 50, 70, 95 (v/v) % ,and the number of cells increased (FIG. 10).

<2-3 >Measurement of Phosphorylated tau in Neuronal Cell Lines

Phosphorylated tau levels were measured in order to confirm the inhibitory effect of *Poria cocos* peel extracts on tau hyper-phosphorylation. SH-SY5Y cells ($1 \times 10^6$ cells/well) were seeded in 6-well culture plates and cultured in DMEM/F12 (Dulbecco's modified Eagle's medium) medium containing 10% FBS (fetal bovine serum) for 48 hours. After 5 days of differentiation using DMEM/F12 medium containing 10 μM retinoic acid and 3% FBS, after 6 hours of treatment with the *Poria cocos* peel extracts (10 or 100 ug/mL), Aβ42 was treated and cultured for a total of 48 hours. After cell lysis using RIPA buffer, the protein content was quantitated with BCA reagent purchased from Pierce. Phosphorylated tau was measured using human Tau [pS199] enzyme-linked immunosorbent assay (ELISA) KIT purchased from Invitrogen.

Figure 11:
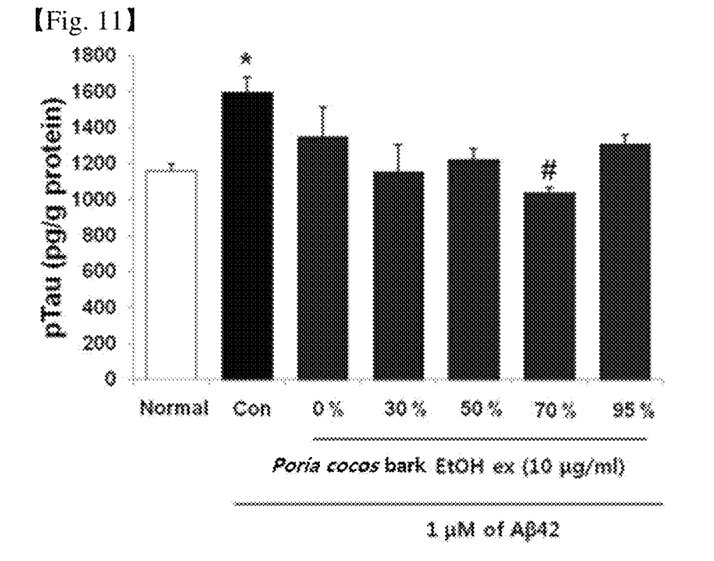
FIG. 11 shows the result of measuring the degree of phosphorylation of tau after treating the neural cell line SH-SY5Y with *Poria cocos* peel extract.

As shown in FIG. 11, when the neuronal cell lines were treated with 10 ug/ml of *Poria cocos* peel ethanol extracts of 0, 30, 50, 70, 95 (v/v), tau phosphorylation induced by $A\beta_{42}$ was suppressed and regained to normal level. Donepezil, which is widely used for dementia, a representative degenerative brain disease, did not show the inhibitory effect on tau phosphorylation (FIG. 11).

<2-4> Nerve Growth Factor (NGF) Level Measurement in Nerve Cell Lines

NGF levels were measured in order to determine the mechanism of cognitive improvement of the *Poria cocos* peel extracts. SH-SY5Y cells (1×106 cells/well) were inoculated on 6-well culture plates and cultured in DMEM/F12 (Dulbecco's modified Eagle's medium) medium containing 10% fetal bovine serum for 48 hours. After 5 days of differentiation using DMEM/F12 medium containing 10 μM retinoic acid and 3% FBS, the cells were treated with *Poria cocos* peel extracts (10 or 100 ug/ml). Cells were lysed using RIPA buffer, and protein content was quantitated with BCA reagent purchased from Pierce. NGF levels were measured using a beta-nerve growth factor human enzyme-linked immunosorbent assay (ELISA) KIT purchased from Abcam.

Figure 12:
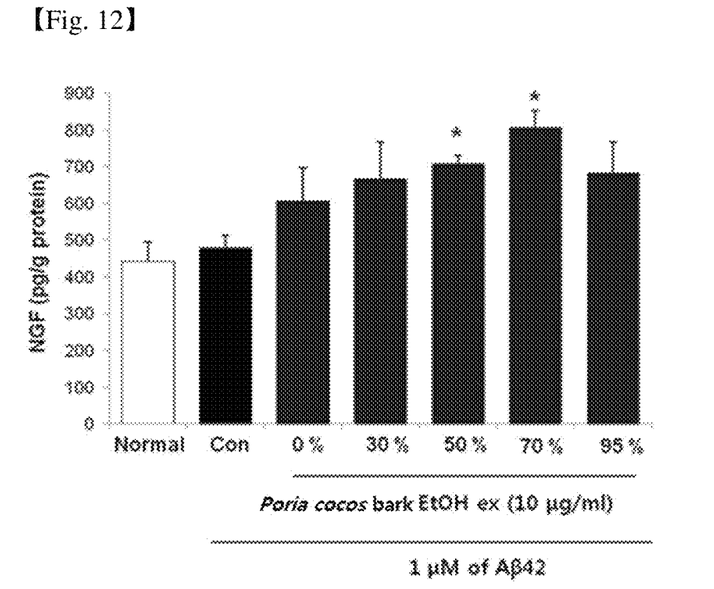
FIG. 12 shows the results of measuring the degree of NGF production after treating the neural cell line SH-SY5Y with *Poria cocos* peel extract.

As shown in FIG. 12, NGF production was significantly increased in the neuronal cell line treated with 10 ug/mL *Poria cocos* peel ethanol extracts of 0, 30, 50, 70, and 95% (v/v). Donepezil, which is widely used for dementia, a typical degenerative brain disease, did not show NGF-related efficacy (FIG. 12).

As described above, *Poria cocos* peel extracts according to the present invention inhibit the onset or progress of the disease by inhibiting beta amyloid production and tau phosphorylation, which cause degenerative brain diseases by causing neuronal cell death, and enhances memory ability by inhibiting acetylcholine esterase. It also promotes the production of NGF, which promotes neuronal protection and neural differentiation. Therefore, the invention can be usefully used for prevention, amelioration and treatment of progressive dementia due to gradual killing of neurons in not only diseases such as Alzheimer dementia, but also Creutzfeldt-Jakob disease, Huntington's disease, multiple sclerosis, Guilin-Barre syndrome, Parkinson's disease, and Lou Gehrig's disease. It may also be useful for the prevention, amelioration and treatment of degenerative neurological disorders including posture and movement disorders, progressive ataxia, muscular atrophy and weakness, and sensory and motor disorders.

Hereinafter, a preparation example of a composition containing the *Poria cocos* peel extracts of Example 1 of the present invention will be described, but this is merely a detailed description of the present invention, and the present invention is not limited thereto.

PREPARATION EXAMPLE 1

Preparation of Injections

| | |
|---|---|
| Example 1 Extract | 100 mg |
| Sodium Metabisulfite | 3.0 mg |
| Methylparaben | 0.8 mg |
| Propylparaben | 0.1 mg |
| Sterilized distilled water for injection | Proper amount |

The above ingredients were mixed and made into 2 ml by the conventional injection preparation method. After that, the mixture was filled in a 2 ml ampoule and sterilized to prepare an injection.

PREPARATION EXAMPLE 2

Preparation of Tablets

| | |
|---|---|
| Example 1 Extract | 200 mg |
| Lactose | 100 mg |
| Starch | 100 mg |
| Magnesium stearate | Proper amount |

The above components are mixed and tablets are prepared by tableting according to the conventional tablet preparation method.

PREPARATION EXAMPLE 3

Preparation of Capsules

| | |
|---|---|
| Example 1 Extract | 100 mg |
| Lactose | 50 mg |
| Starch | 100 mg |
| Talc | 2 mg |
| Magnesium stearate | Proper amount |

The above components are mixed and filled in gelatin capsules according to the conventional preparation method of capsules to prepare capsules.

PREPARATION EXAMPLE 4

Preparation of Liquid Agent

| | |
|---|---|
| Example 1 Ethanol extract | 1000 mg |
| Sugar | 20 g |
| High Fructose Corn | 20 g |
| Lemon incense | Proper amount |
| After adding purified water, the total liquid volume | 100 mL |

The above components were mixed according to the conventional method for producing a liquid preparation, filled in 100 ml of a brown bottle and sterilized to prepare a liquid preparation.

The invention claimed is:

1. A method for treating a degenerative neurological disease in a subject in need thereof, comprising administering to the subject a composition containing an extract of *Poria cocos* peel as an active ingredient;
    wherein the composition does not comprise *Poria cocos* wolf and Jeokbokryeong;
    wherein the degenerative neurological disease is Alzheimer's disease.

2. The method of claim 1, wherein the composition is capable of (i) improving spatial memory, (ii) improving cognitive memory, (iii) protecting nerve cells, (iv) decreasing beta amyloid toxicity in neurons, (v) inhibiting the production of amyloid-β (Abeta), (vi) promoting nerve growth factor production, (vii) inhibiting acetylcholine esterase (AChE) activity, (viii) decreasing $A\beta_{42}$-induced cytotoxicity, (ix) suppressing tau phosphorylation, or (x) any combination thereof.

3. The method of claim 1, wherein the *Poria cocos* peel is extracted with ethanol.

4. The method of claim 1, wherein the extract of *Poria cocos* peel is in an amount of from 10 to 90% by weight based on the total weight of the composition.

5. The method of claim 1, wherein the composition further comprises a suitable carrier, excipient or diluent selected from the group consisting of lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oil.

6. The method of claim 1, wherein the composition is administered orally, intrarectally, intravenously, intramuscularly, subcutaneously, intra-uterine durally, or intracerebroventicularly.

7. The method of claim 1, wherein the composition is administered at a dose of 1.0 mg/kg to 30 mg/kg.

8. The method of claim 1, wherein the composition comprises:
(a) 100 mg of the extract;
(b) 3.0 mg of sodium metabisulfite;
(c) 0.8 mg of methylparaben; and
(d) 0.1 mg of propylparaben;
wherein the composition is in an injectable form.

9. The method of claim 1, wherein the composition comprises:
(a) 200 mg of the extract;
(b) 100 mg of lactose;
(c) 100 mg of starch; and
(d) a pharmaceutically acceptable amount of magnesium stearate;
wherein the composition is in a tablet form.

10. The method of claim 1, wherein the composition comprises:
(a) 100 mg of the extract;
(b) 50 mg of lactose;
(c) 100 mg of starch;
(d) 2 mg of talc; and
(e) a pharmaceutically acceptable amount of magnesium stearate;
wherein the composition is in a capsule form.

11. The method of claim 1, wherein the composition comprises:
(a) 1000 mg of the extract;
(b) 20 g of sugar;
(c) 20 g of high fructose corn; and
(d) a pharmaceutically acceptable amount of lemon incense;
wherein the composition is in a liquid form.

12. The method of claim 1, wherein the composition is administered orally.

13. The method of claim 1, wherein the *Poria cocos* peel is extracted with 60 to 80 percent volume of ethanol/total volume of extract.

14. The method of claim 13, wherein the *Poria cocos* peel is extracted with 70 percent volume of ethanol/total volume of extract.

* * * * *

UNITED STATES PATENT AND TRADEMARK OFFICE
CERTIFICATE OF CORRECTION

PATENT NO. : 10,864,238 B2
APPLICATION NO. : 15/535478
DATED : December 15, 2020
INVENTOR(S) : Choi et al.

It is certified that error appears in the above-identified patent and that said Letters Patent is hereby corrected as shown below:

In the Specification

Column 2, Line 60, delete "Parchymic" and insert -- Pachymic --, therefor.

Column 5, Line 66, delete ".peel" and insert -- peel --, therefor.

Column 9, Line 65, delete "measured" and insert -- measured. --, therefor.

Column 10, Line 53, delete "(FIG. 3, 5)." and insert -- (FIGS. 3, 5). --, therefor.

Column 11, Line 28, delete "Aβ1340" and insert -- $A\beta_{40}$ --, therefor.

Column 12, Line 34, delete "Aβ42." and insert -- $A\beta_{42}$. --, therefor.

Column 12, Line 62, delete "Aβ42" and insert -- $A\beta_{42}$ --, therefor.

In the Claims

Column 15, Claim 6, Lines 14-15, delete "intracerebroventicularly." and insert -- intracerebroventricularly. --, therefor.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*